(12) United States Patent
Chen

(10) Patent No.: US 7,787,197 B2
(45) Date of Patent: Aug. 31, 2010

(54) BEAM-ADJUSTING OPTICS

(75) Inventor: Yong Qin Chen, San Jose, CA (US)

(73) Assignee: Becton, Dickinson and Company, Franklin Lakes, NY (US)

( * ) Notice: Subject to any disclaimer, the term of this patent is extended or adjusted under 35 U.S.C. 154(b) by 112 days.

(21) Appl. No.: 12/231,720

(22) Filed: Sep. 4, 2008

(65) Prior Publication Data
US 2009/0073579 A1 Mar. 19, 2009

Related U.S. Application Data

(60) Provisional application No. 60/993,758, filed on Sep. 14, 2007.

(51) Int. Cl.
*G02B 9/04* (2006.01)
*G02B 9/12* (2006.01)
*G02B 27/64* (2006.01)
*G01N 21/00* (2006.01)

(52) U.S. Cl. ................. 359/793; 359/784; 359/557; 356/338

(58) Field of Classification Search ............ 359/793, 359/794, 554, 557; 356/338
See application file for complete search history.

(56) References Cited

U.S. PATENT DOCUMENTS

| 4,385,834 | A | | 5/1983 | Maxwell, Jr. |
| 4,447,119 | A | * | 5/1984 | Beasley ............... 385/137 |
| 4,989,977 | A | | 2/1991 | North, Jr. |
| 5,077,622 | A | * | 12/1991 | Lynch et al. ............ 359/813 |
| 5,813,987 | A | * | 9/1998 | Modell et al. ............ 600/473 |
| 7,468,789 | B2 | | 12/2008 | Czarnek |
| 7,477,459 | B2 | * | 1/2009 | Liao ..................... 359/773 |
| 7,583,442 | B2 | * | 9/2009 | Cathey et al. ............ 359/558 |
| 7,612,323 | B2 | * | 11/2009 | Okitsu et al. ............ 250/216 |
| 2004/0188393 | A1 | * | 9/2004 | Li et al. ............... 219/121.7 |
| 2005/0112541 | A1 | * | 5/2005 | Durack et al. ............ 435/2 |
| 2008/0144186 | A1 | * | 6/2008 | Feng et al. ............. 359/666 |

OTHER PUBLICATIONS

Hugo Fellner-Feldegg, "Dual laser Flow Cytometry ...," Cytometry, vol. 6: 286-189 (1985.).
J.E. de Josselin de Jong et al., "Alignment and Focusing Unit for Dual-Laser Excitation in the Fluorescent-Activated ...," Cytometry, vol. 5: 657-659 (1984).

* cited by examiner

*Primary Examiner*—Jordan M. Schwartz
(74) *Attorney, Agent, or Firm*—Douglas A. Petry

(57) ABSTRACT

The present invention provides an optical analyzer having illumination optics that include a light source, such as a laser or other source, adapted to emit a collimated, or approximately collimated, light beam, a focusing lens that focuses the beam onto a focus spot within a detection region, and beam-adjusting optics positioned in the light path between the light beam source and the focusing lens, which allow for precise positioning of the focus spot within the detection region. The beam-adjusting optics of the present invention comprise at least one movable focusing lens, mounted in a positioning device that allows repositioning of the lens in a plane perpendicular to the light path.

13 Claims, 4 Drawing Sheets

BEAM-ADJUSTING OPTICS

CROSS-REFERENCE TO RELATED APPLICATIONS

The present application claims priority to U.S. provisional application Ser. No. 60/993,758, filed Sep. 14, 2007, which is incorporated herein by reference in its entirety.

BACKGROUND OF THE INVENTION

1. Field of the Invention

The present invention relates to the field of optics and, in particular, to laser optics, as used in optical analyzers.

2. Description of Related Art

Particle analyzers, such as flow and scanning cytometers, are well known analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, detection is carried out using a multiplicity of photodetectors, one for each distinct dye to be detected. Both flow and scanning cytometers are commercially available from, for example, BD Biosciences (San Jose, Calif.). A full description of flow cytometers is provided in Shapiro, 2003, Practical Flow Cytometry, $4^{th}$ ed. (John Wiley and Sons, Inc. Hoboken, N.J.), and in the references cited therein, all incorporated herein by reference.

In a typical flow cytometer, the excitation light from a laser or other source is focused onto a focal spot to illuminate the core stream (the fluid stream containing the particles to be analyzed). Accurate focusing of the excitation light beam on the core stream is important for optimizing focal spot intensity and, thus, fluorescence sensitivity. Optimal performance is compromised if the focused light beam is not properly adjusted on the core stream, and flow cytometers typically include one or more devices for adjusting the positioning of the focused light beam on the core stream. Because a typical flow cytometer is designed to analyze biological cells or particles that are few microns in size, the precision of the light beam adjustment also needs to be in the micron range, thus requiring high resolution mechanical displacement devices. Conventional positioning methods typically employ expensive differential micrometers to position the light source itself or optical elements, such as mirrors or prisms.

U.S. Pat. No. 4,989,977 describes one device for the accurate adjustment of the focused excitation beam on the core stream. Repositioning of the focal point is achieved using a transparent glass plate located between the focusing lens and the core stream. The glass plate, when positioned at an angle to the beam path, displaces the focal point by refracting the beam. In a multi-laser instrument, the glass plate typically is positioned between the focusing lens and the core stream, and all beams in a multi-laser instrument are passed through the single plate. One disadvantage of this typical implementation is that independent adjustment of the focal spot of each laser is not easily implemented.

BRIEF SUMMARY OF THE INVENTION

The present invention provides illumination optics for use in an optical analyzer that includes a light source, such as a laser or other source, adapted to emit a collimated, or approximately collimated, beam, a focusing lens that focuses the beam onto a focus spot, and beam-adjusting optics positioned in the light path between the light beam source and the focusing lens, which allow for precise positioning of the focus spot of the focused light beam. The beam-adjusting optics of the present invention comprises at least one movable focusing lens, mounted in a positioning device that allows repositioning of the lens in a plane perpendicular to the light path. The size of the movable focusing lens will be sufficiently larger than the width of the collimated beam such that the beam passes through the movable lens when the lens is repositioned.

The present invention further provides an optical analyzer incorporating the illumination optics of the present invention, adapted to focus an illumination beam onto a sample analysis region. The optical analyzer will further comprise detection optics for measuring the light emitted from the analysis region. In a preferred embodiment, the optical analyzer is a flow cytometer, and the sample analysis region is a sample detection region in a fluid stream containing particles to be optically analyzed. Typically, the detection optics detect illumination light scattered by particles in the flow stream, as well as fluorescent light emitted by the particles after being excited by the illumination light.

In one embodiment, the beam-adjusting optics of the present invention comprise a movable beam-adjusting lens that is a long focal length lens, positioned in the optical path such that the optical axis of the lens is parallel to the optical path, wherein the width of the lens is sufficiently larger than the width of the excitation beam to allow for movement of the lens in a plane perpendicular to the optical path while remaining in the optical path.

Increasing the focal length of the movable beam-adjusting lens decreases the sensitivity of the focus spot positioning to changes in the position of the beam-adjusting lens, i.e., increasing the focal length of the movable beam-adjusting lens will decrease the displacement of the focus spot in the sample detection region for a given displacement of the beam-adjusting lens. The decreased sensitivity to movement of the movable beam-adjusting lens allows the use of less expensive, less precise lens positioning mechanisms, such as simple screw-type positioning systems, to obtain precise positioning control over the beam focus spot. As general guidance, the focal length of the movable beam-adjusting lens, minus the distance between the movable beam-adjusting lens and the focusing lens, preferably is at least two times as long as the focal length of the focusing lens, more preferably at least four times as long, and even more preferably, at least six times as long.

Typically, the long-focal length lens is a spherical lens, which allows adjustment of the beam focus spot along both axes perpendicular to the optical path. Depending on the application, it may be sufficient to provide adjustment of the focus spot in only one direction, in which case a cylindrical lens is suitable.

In another embodiment, the beam-adjusting optics of the present invention comprise a converging lens having a positive focal length (e.g., a convex lens) and a diverging lens having a negative focal length (e.g., a concave lens), located a short distance apart other along the optical path and positioned in the optical path such that the optical axis of each lens is parallel to the optical path. At least one of the converging lens and diverging lens is mounted in a positioning device such that the lens can be moved in a plane perpendicular to the optical path, and functions as the beam-adjusting lens. The width of the beam-adjusting length lens is sufficiently larger than the width of the excitation beam to allow for movement of the lens in a plane perpendicular to the optical path while remaining in the optical path. The use of a converging lens along with a diverging lens enables significantly increasing the equivalent focal length of the beam-adjusting optics, which minimizes the effect of the lens pair on the effective focal length of the illumination optics, but which has minimal effect on the beam-adjusting property of the beam-adjusting lens.

In a preferred embodiment, the beam-adjusting optics of the present invention comprise a plano-concave lens and a plano-convex lens, located a short distance apart other along the optical path, positioned in the optical path such that the optical axis of each lens is parallel to the optical path, and oriented such that the concave and convex faces of the lenses are facing each other. At least one of the plano-concave lens and a plano-convex lens is mounted in a positioning device such that the lens can be moved in a plane perpendicular to the optical path, and functions as the beam-adjusting lens. The width of the beam-adjusting length lens is sufficiently larger than the width of the excitation beam to allow for movement of the lens in a plane perpendicular to the optical path while remaining in the optical path.

In a preferred embodiment, the plano-concave lens and the plano-convex lens are matched, i.e., the focal lengths of the lenses are of the same magnitude, but of opposite sign, and the distance between the lens is small, such that parallel light beams entering the beam adjustment optics will exit the beam adjustment optics almost parallel. In this embodiment, the equivalent focal length of the lens pair is much longer than the focal length of the individual lenses, and the lens pair has a negligible effect on the effective focal length of the illumination optics.

In a preferred embodiment, the optical analyzer of the present invention is a flow cytometer and the beam-adjusting optics are component of the illumination (excitation) optics, used to adjust the illumination light focused on the detection region of the flow stream. However, fine control over the focus spot of a illumination beam can be useful in a variety of applications, and the present invention will be generally useful in applications in which fine control over the focus spot of a illumination beam is useful. Other applications in which the illumination optics of the present invention may be useful include, for example, microscopy and laser scanning cytometry.

The beam-adjusting optics of the present invention are particularly suited for use in the illumination light optics of a multi-laser optical analyzer. As the beam adjustment optics can be located anywhere before the focusing lens, individual beam-adjusting optics can be used for each of the lasers in a multi-laser system, thus enabling independent adjustment of the focal spot for each of the lasers.

Figure 1:
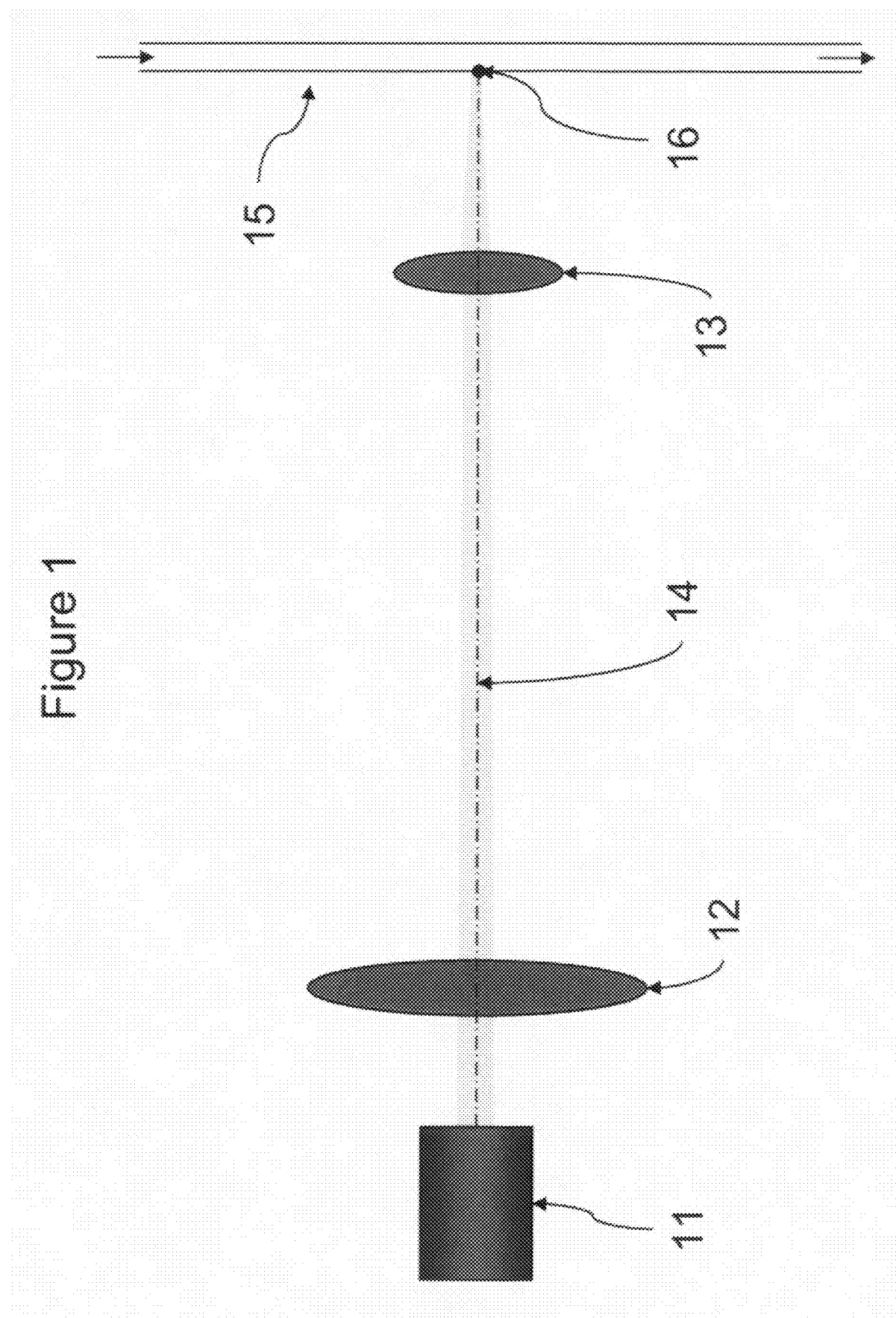
FIG. 1 shows a schematic representation of an embodiment of the illumination optics of the present invention in which the beam-adjusting optics consist of a single long focal length lens.

The figures depict schematic representation of optical systems and are not drawn to scale. The convention in all the figures is that light propagates from left to right through the optical system.

DETAILED DESCRIPTION OF THE INVENTION

The following definitions are provided for clarity. Unless otherwise indicated, all terms are used as is common in the art. All reference cited herein, both supra and infra, are incorporated herein by reference.

As used herein, the "equivalent focal length" or "combined focal length" of a compound optical system refers to the focal length of a compound optical system, given as if it were a single optical element. The equivalent focal length is the distance from the secondary principle point of the compound optical system to the focal point. The equivalent focal length, $f_{eq}$, for a combination of two components is related to the focal lengths of the two components by the following equation:

$$f_{eq} = \frac{f_1 \cdot f_2}{f_1 + f_2 - d}, \qquad (1)$$

wherein $f_1$ and $f_2$ are the focal lengths of the individual components and the d is the distance between the components. The equivalent focal length of a optical system containing more that two components can be calculated by first calculating the equivalent focal length for the first two components, then performing the same calculation using the equivalent focal length for this combination and the focal length of the next lens. This is continued until all lenses in the system are accounted for.

As used herein, the "effective focal length" of a compound optical system refers to the focal length at which an optical system seems to be working in a given situation. The effective focal length is the distance from the secondary principle point of the second (or final) lens to the focal point. The effective focal length for a combination of two components is related to the focal lengths of the two components by the following equation:

$$f_{eff} = \frac{f_2 \cdot (f_1 - d)}{f_1 + f_2 - d}, \qquad (2)$$

wherein $f_1$ and $f_2$ are the focal lengths of the individual components and the d is the distance between the components, or, equivalently, by the following equation:

$$f_{eff} = \frac{f_2}{1 + \frac{f_2}{(f_1 - d)}}. \qquad (3)$$

In many embodiments of the invention, the beam-adjusting optics will consist of one or more "thin lenses". A thin lens is a lens with a thickness (distance along the optical axis between the two surfaces of the lens) that is negligible compared to the focal length of the lens. The optical properties may be approximated using a "thin-lens approximation" in which the thickness of the lens is ignored. Under a thin-lens approximation in which the thickness of the lens is assumed to be zero, the primary and secondary principle points lie in the plane of the lens, and the effective focal length is the distance from the plane of the final lens to the focal point.

Illumination Optics

The illumination optics (also referred to as excitation optics) of the present invention include a light source, such as a laser or other source, adapted to emit a collimated, or approximately collimated, beam, a focusing lens that focuses the beam onto a focus spot, and beam-adjusting optics positioned in the light path between the light beam source and the focusing lens, which allow for precise positioning of the focus spot of the focused light beam. The beam-adjusting optics of the present invention comprises at least one movable focusing lens, mounted in a positioning device that allows repositioning of the lens in a plane perpendicular to the light path. The size of the movable focusing lens will be sufficiently larger than the width of the collimated beam such that the beam passes through the movable lens when the lens is repositioned.

Light Source

Light sources suitable for use in optical analyzers are well known in the art and commercially available from a large number of sources. Example include lasers, arc lamps, and light emitting diodes. For use in the present invention, the emitted light beam should be collimated or approximately collimated. It will be understood that the light source may include collimating optics. A discussion of light sources for use in flow cytometry can be found in, for example, Shapiro, 2003, Practical Flow Cytometry, 4$^{th}$ ed. (John Wiley and Sons, Inc. Hoboken, N.J.), incorporated herein by reference.

Focusing Lens

Focusing lenses are a standard elements well-known in the art and commercially available from a large number of sources. The particular lens design used in the present invention will be application dependent, and one of skill in the art will be able to select a suitable focusing lens routinely following the guidance provided herein. A discussion of focusing lenses for use in flow cytometry can be found in, for example, Shapiro, 2003, Practical Flow Cytometry, 4$^{th}$ ed. (John Wiley and Sons, Inc. Hoboken, N.J.), incorporated herein by reference. Typically, lenses are fabricated of fused silica for maximum light transmission, although any suitable material may be used.

As exemplified herein, a focusing lens typically consists of a single element. However, more complex focusing optics can be used. For example, crossed cylindrical lenses having different focal lengths have been used in flow cytometers to focus a laser beam to an elliptical spot on the sample stream. The focusing optics may additional comprise other elements, such as beam shaping optics, such as described in U.S. Pat. No. 4,498,766 and U.S. Patent Application Publication No. 2006-0256335, both incorporated herein by reference.

Description Based on the Figures

While this invention is satisfied by embodiments in many different forms, shown in the drawings and described herein in detail are preferred embodiments of the invention, with the understanding that the present disclosure is to be considered as exemplary of the principles of the invention and is not intended to limit the invention to the embodiments illustrated.

Single-Lens Beam-Adjusting Optics

FIG. 1 shows a schematic representation of an embodiment of the illumination optics of the present invention in which the beam-adjusting optics consist of a long focal length lens 12 having focal length $f_{12}$. Light source 11, which typically is a laser, emits an essentially collimated beam having an optical path 14, which is focused to focal spot 16 by focusing lens 13 having focal length $f_{13}$. Focal spot 16 corresponds to the detection region in a sample stream 15 containing particles to be optically analyzed. Lens 12 is mounted such that it can be moved in a plane perpendicular to the optical path, such as by using a mechanical positioning system (not shown). In FIG. 1, lens 12 is positioned such that optical path 14 passes through the center of the lens. In this configuration, the focal spot 16 of the illumination optics is not displaced by the beam-adjusting optics from the optical path 14.

Figure 2:
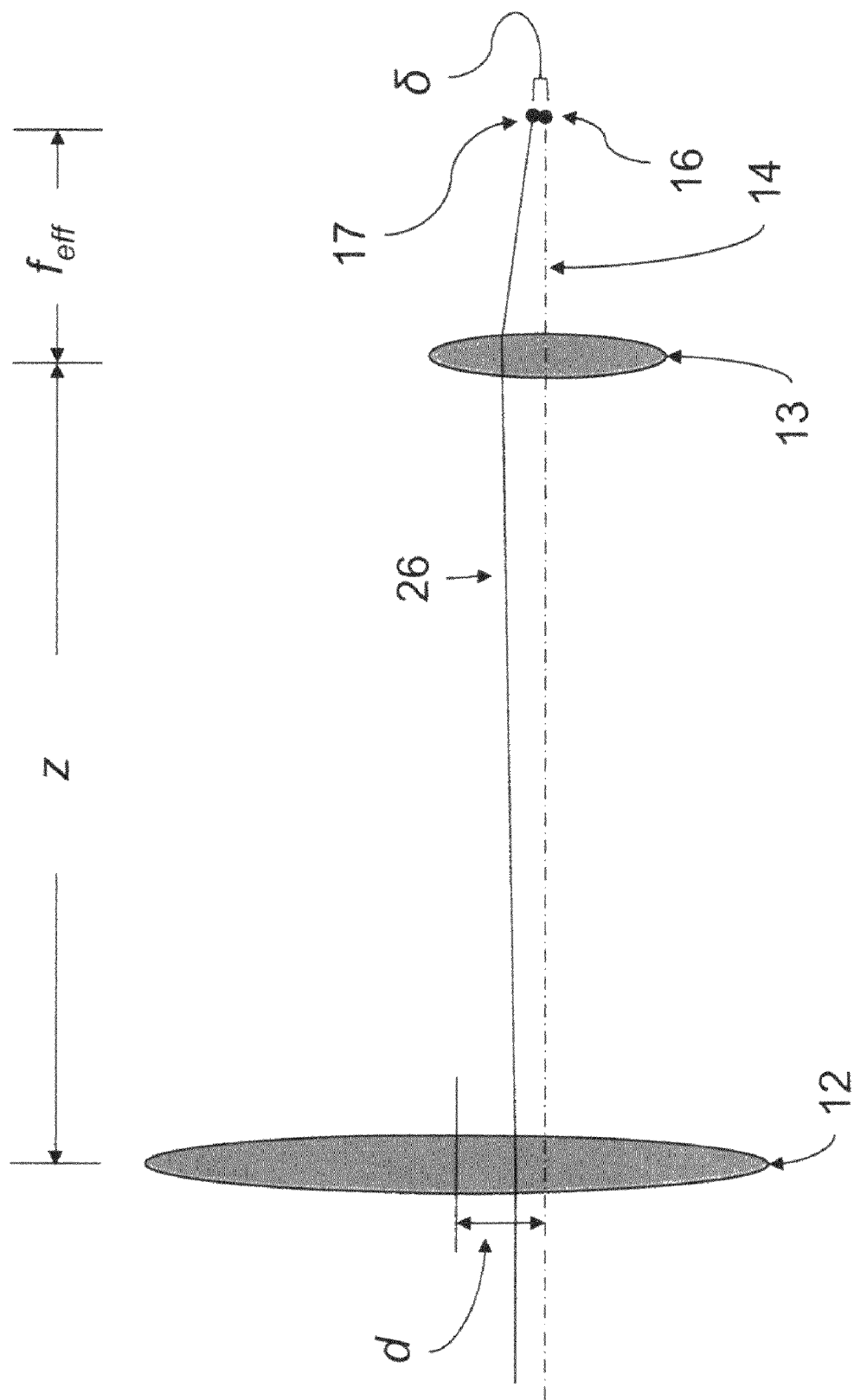
FIG. 2 shows a schematic representation of the path of a light ray through the illumination optics shown in FIG. 1.

FIG. 2 shows a schematic representation of the illumination optics shown in FIG. 1, wherein lens 12 has been displaced by a distance d from the optical path in a plane perpendicular to the optical path. The path of an arbitrary light ray 26 through the beam illumination optics is shown. The optical effect of displacing lens 12 a distance d in a plane perpendicular to the optical path is to move the focal spot to new focal spot 17, displaced from focal spot 16 by a distance δ.

The optical effect of lens 12 on the illumination optics, relative to illumination optics having only focusing lens 13, is two-fold. First, the addition of lens 12 modifies the focal length of the illumination optics. Second, displacement of lens 12 in a plane perpendicular to the optical path displaces the focal point of the illumination optics.

From equation (3), above, the effective focal length, $f_{eff}$, of the illumination optics with lens 12 is $$f_{eff} = \frac{f_{13}}{1 + \frac{f_{13}}{f_{12} - z}}, \tag{4}$$

wherein $f_{12}$ and $f_{13}$ are the focal lengths of lens 12 and lens 13, respectively, and z is the distance between lens 12 and lens 13.

The transverse displacement of the focal point, δ, resulting from displacing lens 12 a distance d in a plane perpendicular to the optical path is $$\delta = \frac{d}{1 + \frac{f_{12} - z}{f_{13}}}. \tag{5}$$

Thus, the beam-adjusting lens allows for a lateral displacement of the focal spot of the illumination optics that is proportional to the displacement of the beam-adjusting lens in a plane perpendicular to the optical-axis. In a preferred embodiment, lens 12 has a focal length much longer than the focal length of lens 13 and the distance between the lenses; more particularly, $|f_{12}-z| \gg f_{13}$. In this embodiment, the displacement of the focal point is approximately $$\delta \approx \frac{d \cdot f_{13}}{(f_{12} - z)}. \tag{6}$$

Given that $|f_{12}-z|\gg f_{13}$, the displacement of the focal spot is greatly reduced relative to the displacement of the beam-adjusting lens 12. This reduced sensitivity of the focal spot adjustment to movement of the beam-adjusting lens enables obtaining a high degree of precision over the adjustment of the focal spot using less expensive lens adjusting mechanisms with less precise motion control.

Preferably, the focal length of lens 12 is such that $|f_{12}-z|\geq 2\cdot f_{13}$, more preferably, $|f_{12}-z|\geq 4\cdot f_{13}$, and even more preferably, $|f_{12}-z|\geq 6\cdot f_{13}$. In general, the preferred focal length of lens 12 and distance z are selected based on the particular application, including the desired focal point adjustment sensitivity and the resolution of the lens adjusting mechanism.

Although FIGS. 1 and 2 depict the focusing optics as a single focusing lens (lens 13), more complex optics may be used, such as, optics having multiple lens elements and, optionally, beam shaping optics, such as described in U.S. Pat. No. 4,498,766 and U.S. Patent Application Publication No. 2006-0256335, both incorporated herein by reference.

Dual-Lens Beam-Adjusting Optics

Figure 3:
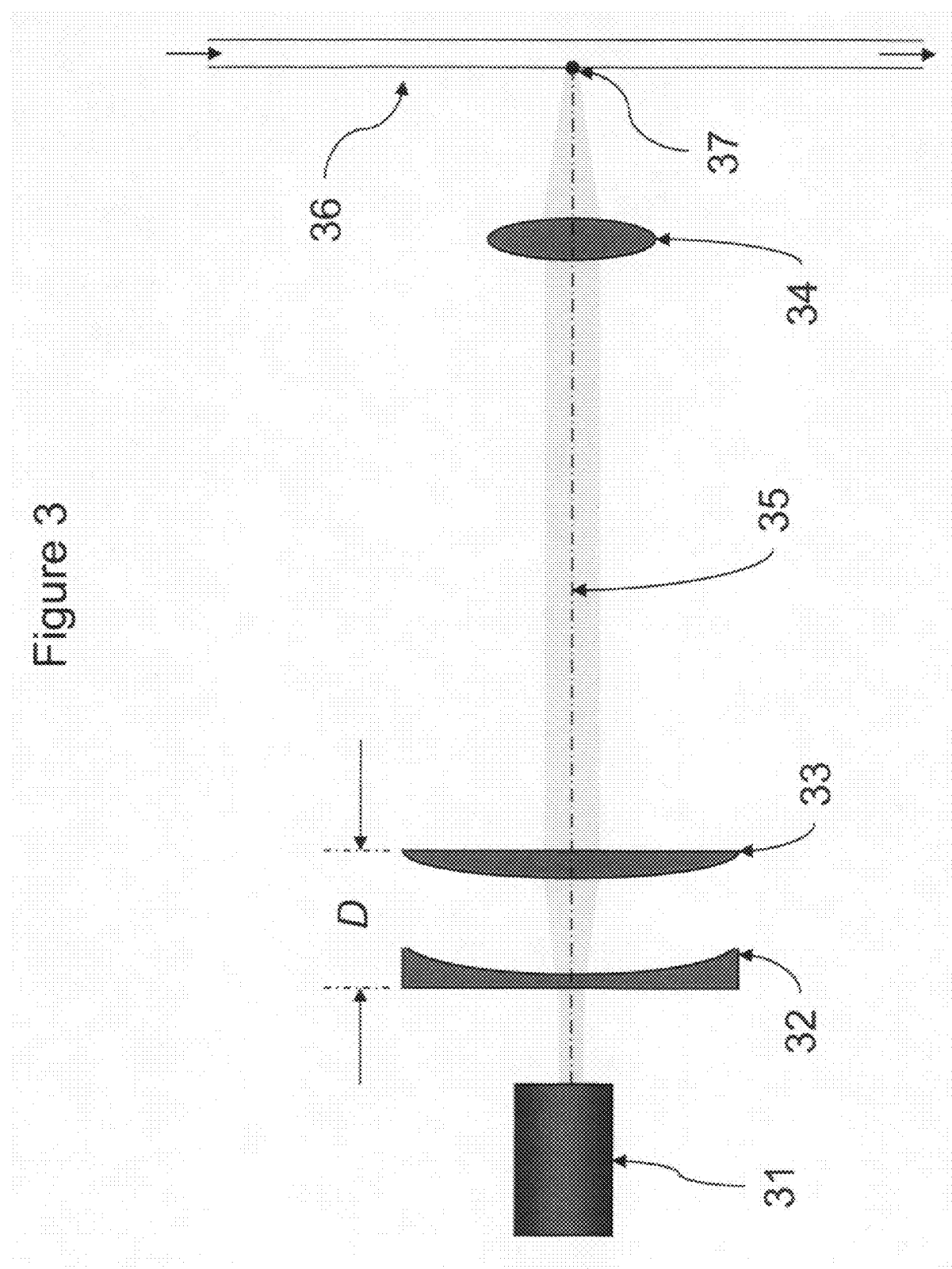
FIG. 3 shows a schematic representation of an embodiment of the illumination optics of the present invention in which the beam-adjusting optics consist of a plano-concave lens and a plano-convex lens.

FIG. 3 shows a schematic representation of an embodiment of the illumination optics of the present invention in which the beam-adjusting optics consist of plano-concave lens 32 and plano-convex lens 33, separated by a distance D. Light source 31 emits a beam having optical path 35, which is focused to a focal spot 37 on the flow stream 36 by focusing lens 34. One of lenses 32 and 33 is mounted such that the lens can be moved in a plane perpendicular to the optical path, such as by using a mechanical positioning system (not shown). In FIG. 3, plano-concave lens 32 and plano-convex lens 33 are positioned such that the optical path is centered in each of the lenses, i.e., the optical axes of the lenses coincides with the optical path. In this configuration, the focal spot 37 of the illumination optics is not displaced by the beam-adjusting optics from the optical path 35.

Figure 4:
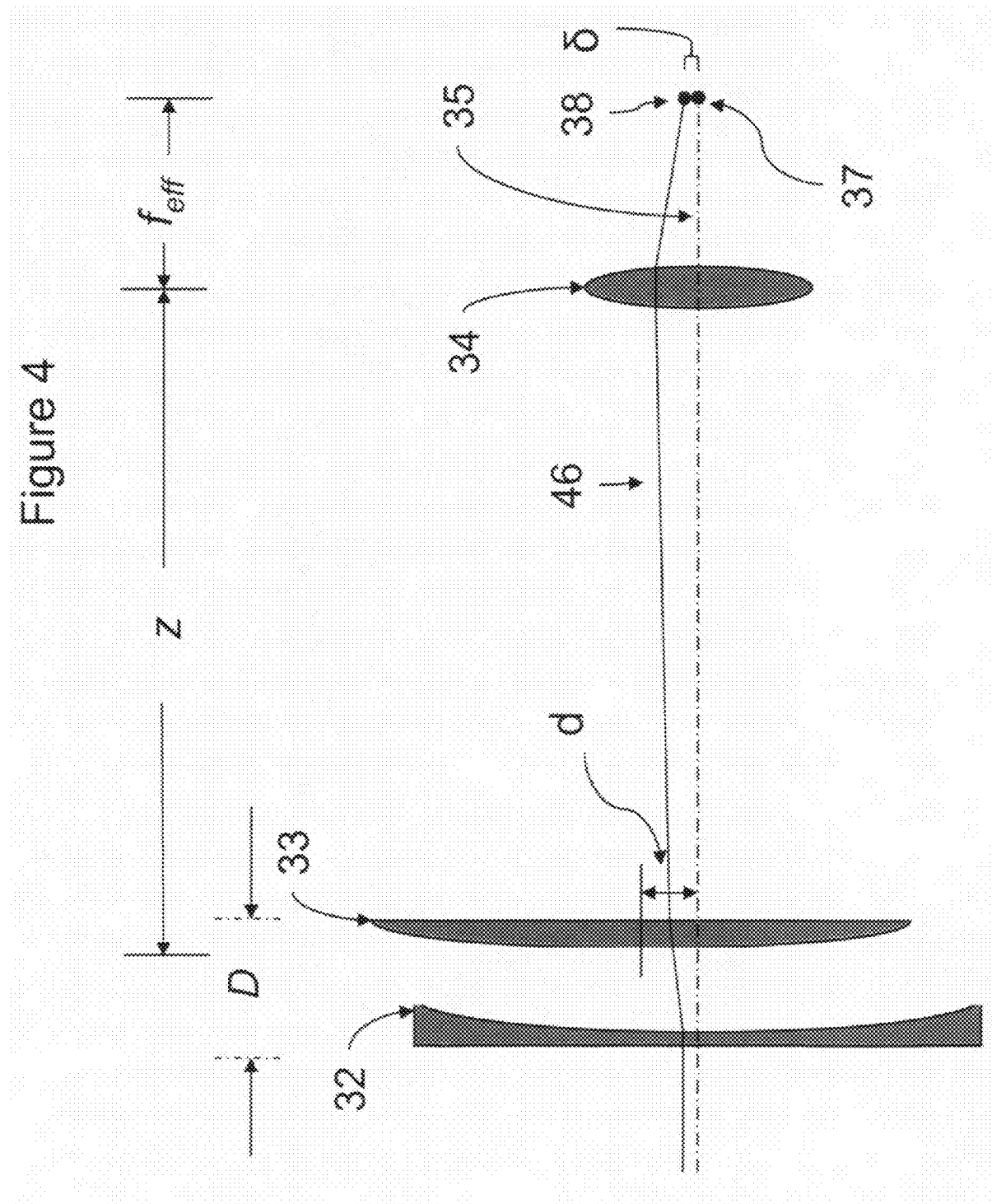
FIG. 4 shows a schematic representation of the path of a light ray through the illumination optics shown in FIG. 3.

FIG. 4 shows a schematic representation of the beam illumination optics shown in FIG. 3, wherein lens 33 has been displaced by a distance d from the optical path in a plane perpendicular to the optical path. The path of an arbitrary light ray 46 through the beam illumination optics is shown.

The optical effect of lens pair 32 and 33 on the illumination optics, relative to illumination optics having only focusing lens 34, is two-fold. First, the addition of lens pair 32 and 33 modifies the focal length of the illumination optics. Second, displacement of one of the lenses of lens pair 32 and 33 in a plane perpendicular to the optical path displaces the focal point of the illumination optics.

From equation (1), above, the equivalent focal length, $f_{eq}$, of the lens pair 32 and 33 is $$f_{eq} = \frac{f_{32}\cdot f_{33}}{f_{32}+f_{33}-D}, \tag{7}$$

wherein $f_{32}$ and $f_{33}$ are the focal lengths of lens 32 and lens 33, respectively, and D is the distance between lens 32 and lens 33.

From equation (3), above, the effective focal length, $f_{eff}$, of the illumination optics with lens pair 32 and 33 is $$f_{eff} = \frac{f_{34}}{1+\frac{f_{34}}{f_{eq}-z}}, \tag{8}$$

wherein $f_{34}$ is the focal length of lens 34, and z is the distance between second primary point of the lens pair 32 and 33 and lens 34.

In a preferred embodiment, lenses 32 and 33 are matched, by which is meant that $f_{32}=-f_{33}$, and lenses 32 and 33 are separated by a small distance relative to the focal length of the lenses, i.e., $D\ll|f_{32}|$ and $D\ll|f_{33}|$. In this embodiment, $$f_{eq} \approx \frac{-f_{32}^2}{D}, \tag{9}$$

and, thus, the equivalent focal length of the lens pair is much longer than the focal length of the individual lenses. Furthermore, equation (8) shows that, in this embodiment, the lens pair will have a negligible effect on the effective focal length of the illumination optics.

The displacement of the focal spot induced by a displacement of one of the lenses of the lens pair 32 and 33 can be obtained from an analysis of the optical property of the lens pair on the path of light ray 46 using the well-known ray tracing technique of ray transfer matrix analysis (see, for example, Warren J. Smith, 1996, Modern Optical Engineering: The Design of Optical Systems, $2^{nd}$ Ed. (McGraw-Hill, Inc., New York, N.Y.), incorporated herein by reference). In ray transfer matrix analysis (also known as ABCD matrix analysis), an optical system (e.g., one or more lenses) is described using a ray transfer matrix, and a vector representing the light ray leaving the system is determined by multiplying the ray transfer matrix with a vector representing the light ray entering the system. The technique uses the paraxial approximation of ray optics in which a ray is assumed to be at a small angle ($\theta$) to the optical axis of the system and remain at a small distance (x) from the optical axis of the system. This allows the approximations $\sin(\theta)\approx\theta$, $\tan(\theta)\approx\theta$, and $\cos(\theta)\approx 1$ (where $\theta$ is measured in radians) to be used in the calculation of the ray's path. A thin-lens approximation (see above) is also used in the following analysis.

In ray transfer matrix analysis, an arbitrary paraxial light ray is specified by the vector $$\begin{pmatrix} x \\ \theta \end{pmatrix},$$

wherein x is the distance of the ray from the optical axis, and $\theta$ is the angle between the ray and the optical axis. The ray vector after passing through an optical system, denoted by $$\begin{pmatrix} x' \\ \theta' \end{pmatrix},$$

is then $$\begin{pmatrix} x' \\ \theta' \end{pmatrix} = S \begin{pmatrix} x \\ \theta \end{pmatrix},$$

wherein S is the ray transfer matrix for the optical system.

For a paraxial ray impinging upon a thin lens of focal length f that is displaced a distance d from the optical axis of the beam, $$\begin{pmatrix} x' \\ \theta' \end{pmatrix} = \begin{pmatrix} 1 & 0 \\ -1/f & 1 \end{pmatrix} \begin{pmatrix} x \\ \theta \end{pmatrix} + \begin{pmatrix} 0 \\ -d/f \end{pmatrix}.$$

Denote the focal lengths of lenses 32 and 33 as $f_{32}$ and $f_{33}$, respectively. Then, for a paraxial ray impinging on lens pair 32 and 33, separated by a distance D, where lens 33 is displaced d from the optical axis, $$\begin{pmatrix} x' \\ \theta' \end{pmatrix} = \begin{pmatrix} 1 & 0 \\ -1/f_{33} & 1 \end{pmatrix} \begin{pmatrix} 1 & D \\ 0 & 1 \end{pmatrix} \begin{pmatrix} 1 & 0 \\ -1/f_{32} & 1 \end{pmatrix} \begin{pmatrix} x \\ \theta \end{pmatrix} + \begin{pmatrix} 0 \\ d/f_{33} \end{pmatrix}.$$

In a preferred embodiment, lenses 32 and 33 are matched, by which is meant that $f_{32} = -f_{33}$, and lenses 32 and 33 are separated by a small distance relative to the focal length of the lenses, i.e., $D \ll |f_{32}|$ and $D \ll |f_{33}|$. In this embodiment, any ray that is nearly parallel to the optical axis (i.e., for which $\theta \approx 0$) will then be transformed by the lens pair into $$x' \approx (1 + D/f_{33}) \cdot x \qquad (10)$$

$$\theta' \approx d/f_{33}$$

The angular displacement induced by the lens pair, given in equation (10), above, causes a displacement, δ, of the focal spot of the illumination optics, where $$\delta = f_{34} \cdot \theta' \approx \frac{f_{34} \cdot d}{f_{33}}. \qquad (11)$$

Using long focal length lenses 32 and 33, such that that $f_{34}/f_{33} \ll 1$, the displacement of the focal spot is greatly reduced relative to the displacement of the beam-adjusting lens 33. This reduced sensitivity of the focal spot adjustment to movement of the beam-adjusting lens enables obtaining a high degree of precision over the adjustment of the focal spot using less expensive lens adjusting mechanisms with less precise motion control.

I claim:

1. An optical analyzer comprising:
   (a) a light source adapted to emit an approximately collimated light beam along a light path;
   (b) a focusing lens positioned in the light path, adapted to focus the light beam onto a focal spot within a sample analysis region, wherein said focusing lens has a focal length $f_1$,
   (c) beam-adjusting optics positioned in the light path between the light source and the focusing lens, wherein said beam-adjusting optics comprises at least one beam-adjusting lens that is mounted in a positioning device that allows movement of the beam-adjusting lens in a plane perpendicular to the light path, wherein said beam-adjusting lens has a focal length $f_2$, wherein said beam-adjusting lens and said focusing lens are separated by a distance z along the light path, and wherein $|f_2 - z| \geq 4 \cdot f_1$.

2. The optical analyzer of claim 1, wherein $|f_2 - z| \geq 6 \cdot f_1$.

3. The optical analyzer of claim 1, wherein said beam-adjusting lens is a spherical lens.

4. The optical analyzer of claim 1, wherein said beam-adjusting lens is a cylindrical lens.

5. An optical analyzer comprising:
   (a) a light source adapted to emit an approximately collimated light beam along a light path;
   (b) a focusing lens positioned in the light path, adapted to focus the light beam onto a focal spot within a sample analysis region, wherein said focusing lens has a focal length $f_1$,
   (c) beam-adjusting optics positioned in the light path between the light source and the focusing lens, wherein said beam-adjusting optics comprises at least one beam-adjusting lens that is mounted in a positioning device that allows movement of the beam-adjusting lens in a plane perpendicular to the light path, wherein said beam-adjusting optics comprise a divergent lens having a focal length $f_2$, wherein $f_2$ is negative, and a convergent lens having a focal length $f_3$, wherein $f_3$ is positive, wherein said beam-adjusting lens is said divergent lens or said convergent lens, wherein $f_2 = -f_3$.

6. An optical analyzer comprising:
   (a) a light source adapted to emit an approximately collimated light beam along a light path;
   (b) a focusing lens positioned in the light path, adapted to focus the light beam onto a focal spot within a sample analysis region, wherein said focusing lens has a focal length $f_1$,
   (c) beam-adjusting optics positioned in the light path between the light source and the focusing lens, wherein said beam-adjusting optics comprises at least one beam-adjusting lens that is mounted in a positioning device that allows movement of the beam-adjusting lens in a plane perpendicular to the light path, wherein said beam-adjusting optics comprise a plano-concave lens having a focal length $f_2$ and a plano-convex lens having a focal length $f_3$, wherein said beam-adjusting lens is said plano-concave lens of said plano-convex lens.

7. The optical analyzer of claim 6, wherein $f_2 \geq 2 \cdot f_1$ and $-f_3 \geq 2 \cdot f_1$.

8. The optical analyzer of claim 6, wherein $f_2 \geq 4 \cdot f_1$ and $-f_3 \geq 4 \cdot f_1$.

9. The optical analyzer of claim 6, wherein $f_2 \geq 6 \cdot f_1$ and $-f_3 \geq 6 \cdot f_1$.

10. The optical analyzer of claim 6, wherein $f_2 = -f_3$.

11. The optical analyzer of claim 10, wherein $f_2 \geq 2 \cdot f_1$.

12. The optical analyzer of claim 10, wherein $f_2 \geq 4 \cdot f_1$.

13. The optical analyzer of claim 10, wherein $f_2 \geq 6 \cdot f_1$.

* * * * *